(12) United States Patent
Kuan et al.

(10) Patent No.: US 8,519,333 B2
(45) Date of Patent: Aug. 27, 2013

(54) CHARGED PARTICLE SYSTEM FOR RETICLE/WAFER DEFECTS INSPECTION AND REVIEW

(75) Inventors: Chiyan Kuan, Danville, CA (US);
Yi-Xiang Wang, Fremont, CA (US);
Chung-Shih Pan, Palo Alto, CA (US);
Zhonghua Dong, Sunnyvale, CA (US);
Zhongwei Chen, San Jose, CA (US)

(73) Assignee: Hermes Microvision Inc., Hsinchu (TW)

( * ) Notice: Subject to any disclaimer, the term of this patent is extended or adjusted under 35 U.S.C. 154(b) by 0 days.

(21) Appl. No.: 13/463,208

(22) Filed: May 3, 2012

(65) Prior Publication Data

US 2012/0280125 A1 Nov. 8, 2012

Related U.S. Application Data

(60) Provisional application No. 61/482,084, filed on May 3, 2011.

(51) Int. Cl.
*H01J 37/20* (2006.01)
*H01J 37/26* (2006.01)
*G01N 23/225* (2006.01)
*G01N 23/22* (2006.01)

(52) U.S. Cl.
USPC ............ 250/310; 250/306; 250/607; 250/311

(58) Field of Classification Search
USPC .......................... 250/306, 307, 308, 310, 311
See application file for complete search history.

(56) References Cited

U.S. PATENT DOCUMENTS

| | | | | |
|---|---|---|---|---|
| 6,184,526 | B1 * | 2/2001 | Kohama et al. | 250/310 |
| 7,202,476 | B2 * | 4/2007 | Suga et al. | 250/310 |
| 7,906,760 | B2 * | 3/2011 | Nishiyama et al. | 250/307 |
| 7,923,700 | B2 * | 4/2011 | Nishiyama | 250/440.11 |
| 8,030,622 | B2 * | 10/2011 | Nishiyama et al. | 250/440.11 |
| 8,119,994 | B2 * | 2/2012 | Nishiyama et al. | 250/440.11 |
| 8,158,937 | B2 * | 4/2012 | Koizumi et al. | 250/306 |
| 8,294,095 | B2 * | 10/2012 | Chen et al. | 250/310 |
| 2009/0242762 | A1 * | 10/2009 | Nishiyama et al. | 250/307 |
| 2009/0250609 | A1 * | 10/2009 | Nishiyama et al. | 250/306 |
| 2009/0314955 | A1 * | 12/2009 | Nishiyama et al. | 250/442.11 |
| 2010/0019146 | A1 * | 1/2010 | Nishiyama et al. | 250/307 |
| 2010/0051803 | A1 * | 3/2010 | Koizumi et al. | 250/306 |
| 2010/0096549 | A1 * | 4/2010 | Nishiyama | 250/307 |
| 2010/0181480 | A1 * | 7/2010 | Shimakura et al. | 250/310 |
| 2010/0243888 | A1 * | 9/2010 | Nishiyama et al. | 250/307 |
| 2012/0280125 | A1 * | 11/2012 | Kuan et al. | 250/310 |

* cited by examiner

*Primary Examiner* — David A Vanore
(74) *Attorney, Agent, or Firm* — WPAT, PC; Justin King

(57) ABSTRACT

The present invention relates to a charged particle system for reticle or semiconductor wafer defects inspection and review, and more particularly, relates to an E-beam inspection tool for reticle or semiconductor wafer defects inspection and review without gravitational AMC settling. The charged particle system is an upside down electron beam inspection system with an electron beam aimed upward. The face down design may prevent AMC from gravitational settling on the inspected face of the specimen during inspection, thereafter having a cleaner result compared with conventional face-up inspection system.

22 Claims, 8 Drawing Sheets

CHARGED PARTICLE SYSTEM FOR RETICLE/WAFER DEFECTS INSPECTION AND REVIEW

CROSS-REFERENCE TO RELATED APPLICATIONS

This application claims the benefit of U.S. Provisional Application No. 61/482,084, filed on May 3, 2011 and entitled CHARGED PARTICLE SYSTEM FOR RETICLE/WAFER DEFECTS INSPECTION AND REVIEW, the entire contents of which are hereby incorporated by reference.

FIELD OF THE INVENTION

The present invention relates to a charged particle system for reticle or semiconductor wafer defects inspection and review, and more particularly, relates to an E-beam inspection tool for reticle or semiconductor wafer defects inspection and review without gravitational AMC settling. However, it would be recognized that the invention has a much broader range of applicability.

BACKGROUND OF THE INVENTION

Defect inspection of semiconductor wafers and reticles (masks) for IC manufacturing is an accepted production process for yield enhancement. The information obtained from a wafer defect inspection tool can be used to flag defective dies for repair, or improve wafer processing parameters. Since a single mask can be used in production of hundreds or even thousands of wafers, therefore, an undetected error or defect in the mask can cause significant loss in yield.

Mask defects are commonly divided into two different categories: hard and soft defects. A defect is called hard defect if it is not possible to be removed by a cleaning process. Added or missing features in the chrome, phase shifter, pin-dots, scratches, bubbles as well as pinholes fall in this category. A defect is called a soft defect if it can be removed by a cleaning process. Particles, stains, contaminations such as crystals, and residual materials are soft defects. All the hard defects need to be located, fixed, and/or corrected in processes. Although soft defects are removable with a cleaning process, however, accidentally deposited particles on the reticle over a critical size may result in a fatal defect in every die of the wafer, corresponding to zero yield. Therefore in conventional lithography or optical defect inspection process, the reticle is protected with pellicle on the backside to prevent soft defects deposition during process.

In the Extreme Ultra-Violet (EUV) lithography process, this technology is based on 13.5 nm wavelength. However because of high material absorption of this wavelength, EUV reticles do not have a protective pellicle in proximity of the surface to prevent particles from accidentally falling on the pattern area especially during handling and exposure. Stringent specifications are required to ensure that practically no particle is present at the time of exposure.

In the electron beam inspection practice, no matter inspecting conventional wafers, reticles or EUV masks, no protective pellicle can be used. Therefore, preventing soft defects from contaminating the inspected objective surface during inspection practice should be considered seriously.

The present invention restructures the charged particle system to avoid gravitational settling on inspected surface, thereafter meeting the stringent specification for the advanced defects inspection and review.

SUMMARY OF THE INVENTION

One embodiment of the present invention discloses an operation stage that sustains a face-down mounting of the inspected object on the operation stage to avoid AMC falling on inspected surface during defects inspection.

One embodiment of the present invention discloses an electron beam inspection system with an upside down SORIL lens column and the new operation stage. The primary beam aimed up to the face-downed inspected object, wherein the inspected object is a wafer, a reticle for regular lithography or an EUV mask.

Another embodiment of the present invention discloses an electron beam inspection. system with an upside down multi-axial lens column and the new operation stage. Primary beam of each electron source for each sub-lens within the multi-axial lens aimed up to the face-downed inspected object.

The upside down inspection system is equipped with a multi-axial lens column to gain throughput in addition to the benefit of preventing AMC contamination during inspection.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF THE INVENTION

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations are not described in detail in order not to unnecessarily obscure the present invention.

Figure 1:
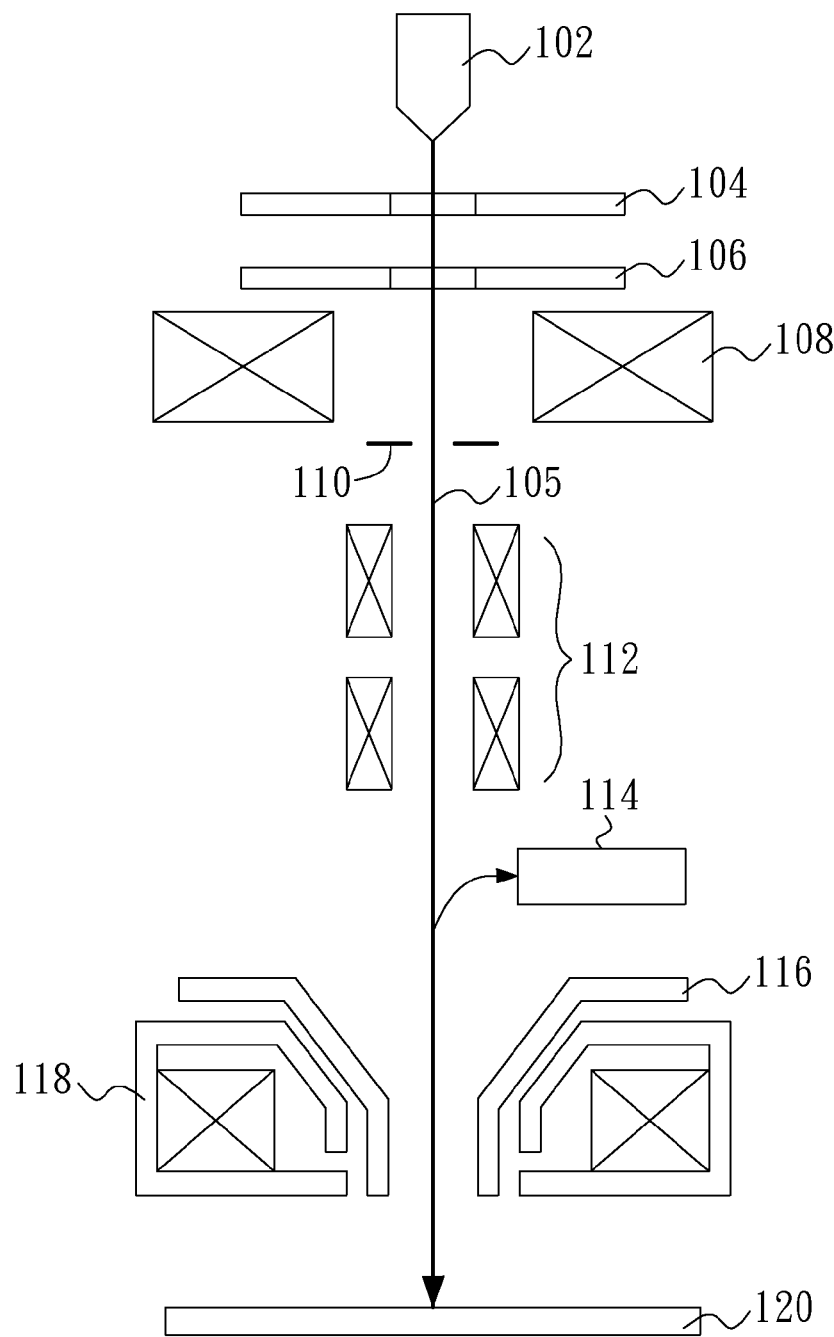
FIG. 1 is a schematic diagrammatic representation of a conventional e-beam inspection system.

FIG. 1 is a schematic diagrammatic representation of a conventional e-beam inspection system 100. The conventional e-beam inspection system 100 includes an electron source (e gun) 102 for emitting an electron beam 105, an extractor 104, an anode 106, a condenser lens 108, a beam aperture 110, a detector 114 for receiving secondary electrons emanating from the surface of a specimen 120, and an objective lens wherein the objective lens includes deflectors 112, a magnetic lens 118 and an electrostatic lens (acceleration tube) 116 inside the objective lens. The conventional e-beam inspection system 100 performs inspection with the electron source 102 at the top portion of the system 100 and the inspected object (or specimen) 120 that sit on an operation stage facing up to the electron source 102 as FIG. 1 illustrated.

A face-up inspected objective (or specimen) surface cannot prevent airborne molecular contaminates (AMC) from accidentally falling on the patterned surface. It is found that inspected surface upside down is an effective way to avoid gravitational AMC settling. Therefore, the present invention provides a new operation stage and a new E-beam inspection tool which can sustain a face-down configuration for mounting the object to be inspected on the operation stage to avoid AMC falling on the inspected surface during defects inspection.

One embodiment of the present invention discloses an operation stage that sustains a face-down configuration for mounting the inspected object on the operation stage to avoid AMC falling on the inspected surface of the inspected object during defects inspection.

Figure 2:
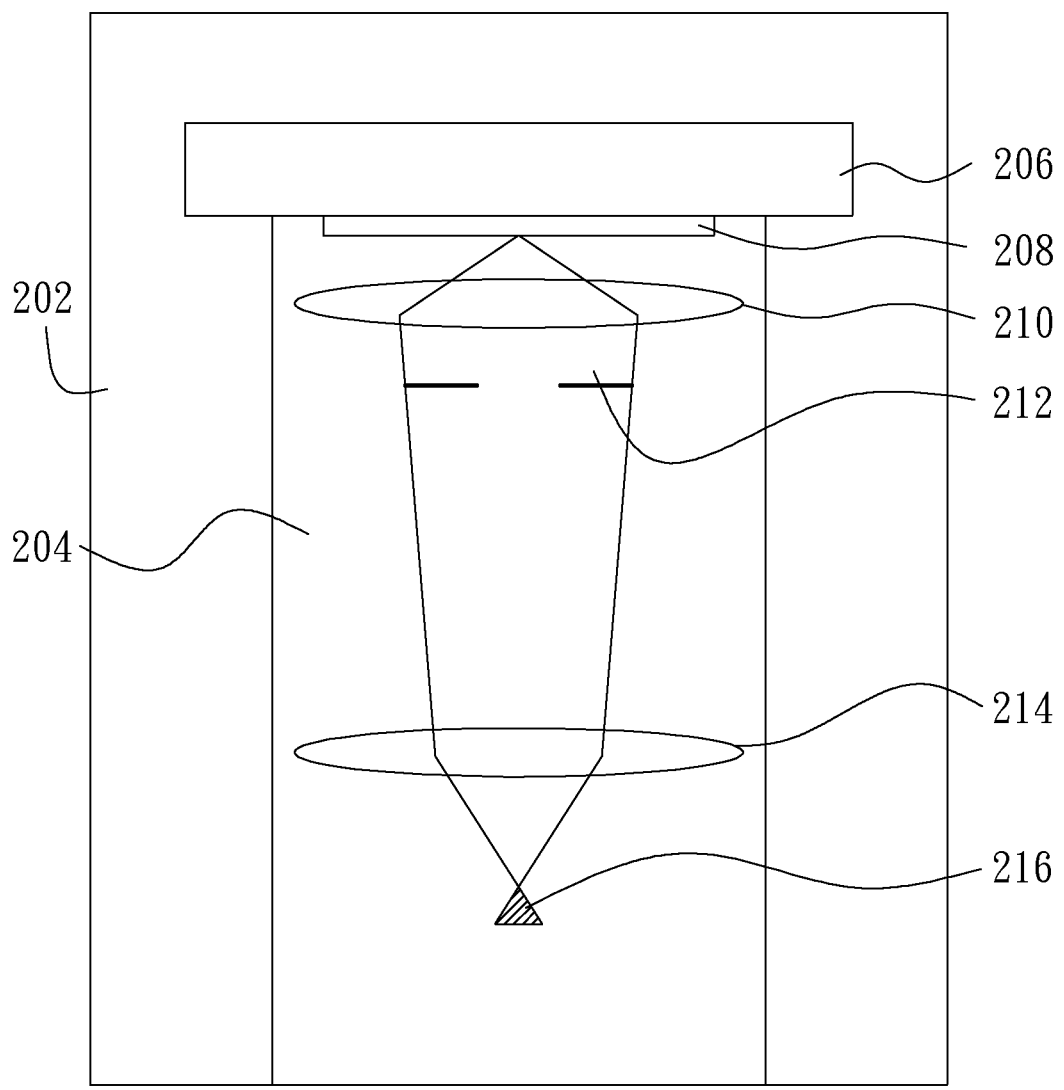
FIG. 2 is a schematic diagrammatic representation of an aimed-up charged particle beam system in accordance with an embodiment of the present invention.

Referring to FIG. 2, it is a schematic diagrammatic representation of an aimed-up charged particle beam system 200, for example an e-beam inspection system, in accordance with an embodiment of the present invention. The aimed-up charged particle beam system 200 is an upside down charged particle beam inspection system with a charged particle beam aimed upward. The aimed-up charged particle beam system 200 includes an electron source 216, a condenser lens 214, a detector 212, an objective lens 210, and an operation stage 206. The electron source 216 is configured at the bottom of the aimed-up charged particle beam system 200 for providing a primary beam upward. The operation stage 206 is configured at the top of the aimed-up charged particle beam system 200 for holding a specimen 208, such as a reticle or a wafer, upside down and the inspected surface of the specimen 208 facing downward to the primary beam, such that particles nearby will not drop to the inspected surface of the specimen 208. The condenser lens 214 is configured over the electron source 216 for condensing the primary beam. The objective lens 210 is configured over the condenser lens 214 for focusing the primary beam to the inspected surface of the specimen 208. The condenser lens 214 and the objective lens 210 are configured between the electron source 216 and the operation stage 206, and the detector 212 can be configured between the condenser lens 214 and the objective lens 210, for receiving secondary electrons emanating from the surface of the specimen 208. In the aimed-up charged particle beam system 200, the electron source 216 sits on the bottom of the system 200 to emit the charged particle beam (such as electron beam) upward and the specimen 208 is held or hung on the top of the system 200 with the inspected surface of the specimen 208 facing downward to the electron source 216. The electron beam is emitted from the bottom of the system 200 upward to the top of the system 200. The face down design may prevent AMC from gravitationally settling during inspection, thereafter having a cleaner result compared with conventional face-up inspection system.

The electron source 216, the condenser lens 214, the detector 212, and the objective lens 210 are configured inside a column 204, and the electron source 216, the condenser lens 214, the detector 212, the objective lens 210, and the operation stage 206 are inside a vacuum chamber 202 for reducing the particles in the system 200. In other words, the column 204 is inside the vacuum chamber 202, and both of the column 204 and the vacuum chamber 202 are in a vacuum environment. The aimed-up charged particle beam system 200 provides a vacuum environment during inspection. Therefore, the gravitational settling of AMC during inspection can be avoided.

Figure 3:
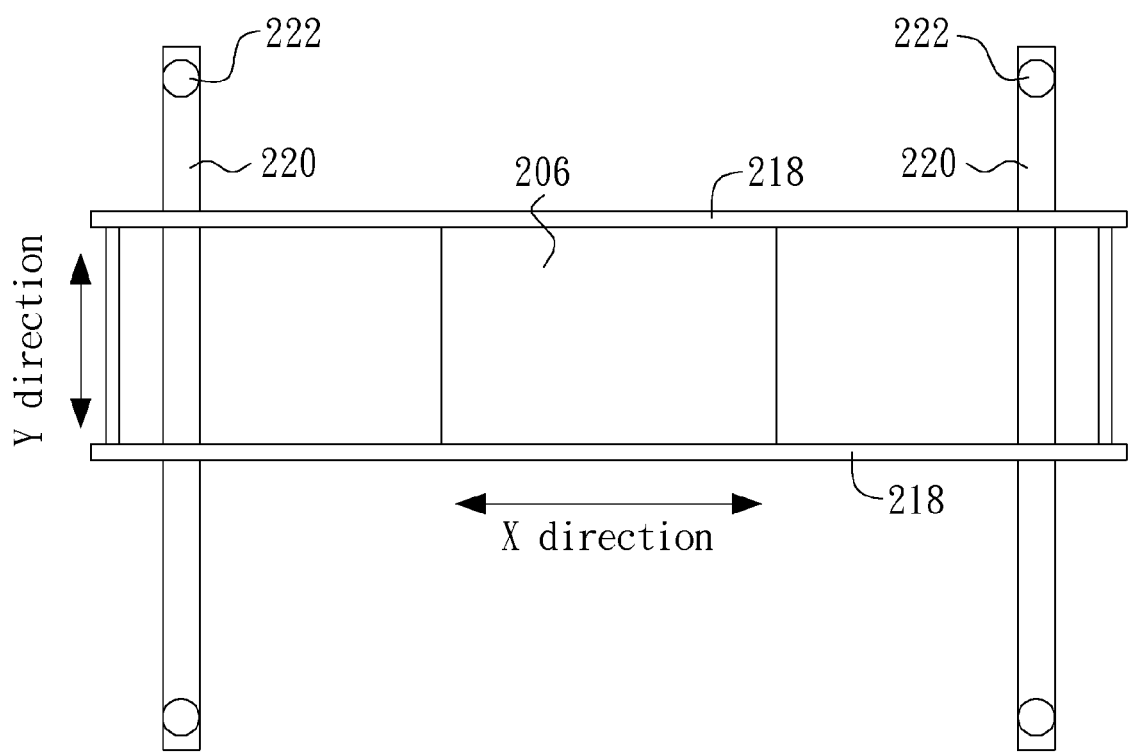
FIG. 3 is a schematic diagrammatic representation of a top view of a new designed operation stage illustrated in FIG. 2 that sustains a face-down reticle or wafer to be inspected.

In the system 200, the operation stage 206 can move in X direction and Y direction for moving the specimen 208 to inspect different areas on the surface of the specimen 208. The present invention provides two designs for moving the operation stage 206. FIGS. 2-3 and FIGS. 4-5 illustrate the two designs respectively. FIG. 3 is a schematic diagrammatic representation of a top view of an operation stage that sustains a face-down reticle or wafer to be inspected in accordance with an embodiment of the present invention as illustrated in FIG. 2. Referring to FIG. 2 and FIG. 3, in aimed-up charged particle beam system 200, there are a pair X direction sliders 218 for moving the operation stage 206 on X direction and a pair of Y direction sliders 220 for moving the operation stage 206 on Y direction. The four sliders 218, 220 provide the operation stage 206 that moves freely on X and Y direction during operation. The X direction slider 218, the Y direction slider 220, and the operation stage 206 are supported by a supporting means 222, and they are held or hung at the top of the aimed-up charged particle beam system 200 by the supporting means 222. The supporting means 222 is mounted on the solid foundation of the aimed-up charged particle beam system 200. Although the supporting means 222 includes four pillars in FIG. 3, it is not limited to this. In other embodiment of the present invention, the supporting means may include several pillars (at least three pillars), for example three pillars, four pillars or more, or the supporting means may be a hollow cylinder which the aimed-up charged particle beam system 200 (including the vacuum chamber 202 and column 204) is configured inside.

Figure 4:
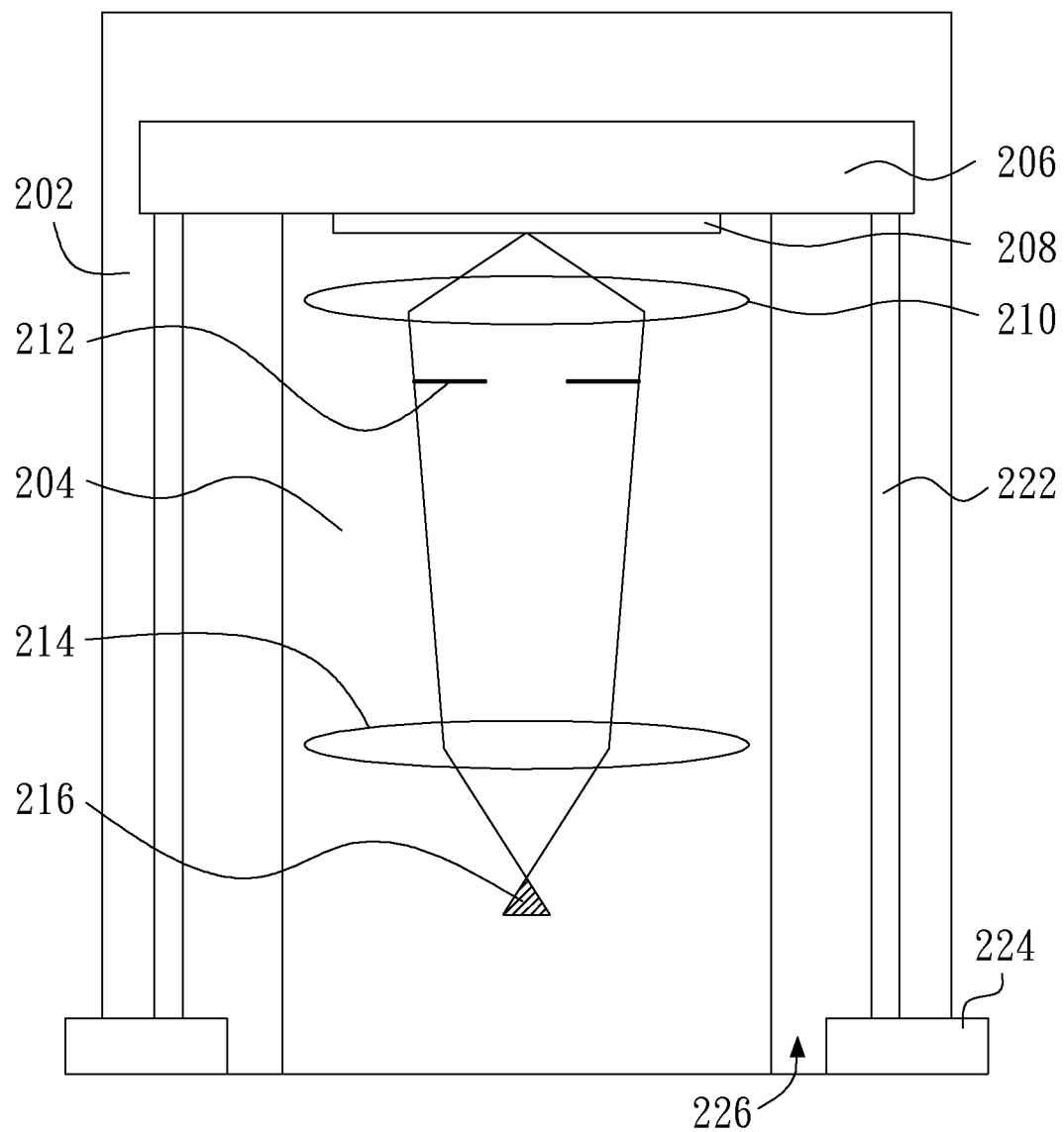
FIG. 4 is a schematic diagrammatic representation of another aimed-up charged particle beam system in accordance with another embodiment of the present invention.
Figure 5:
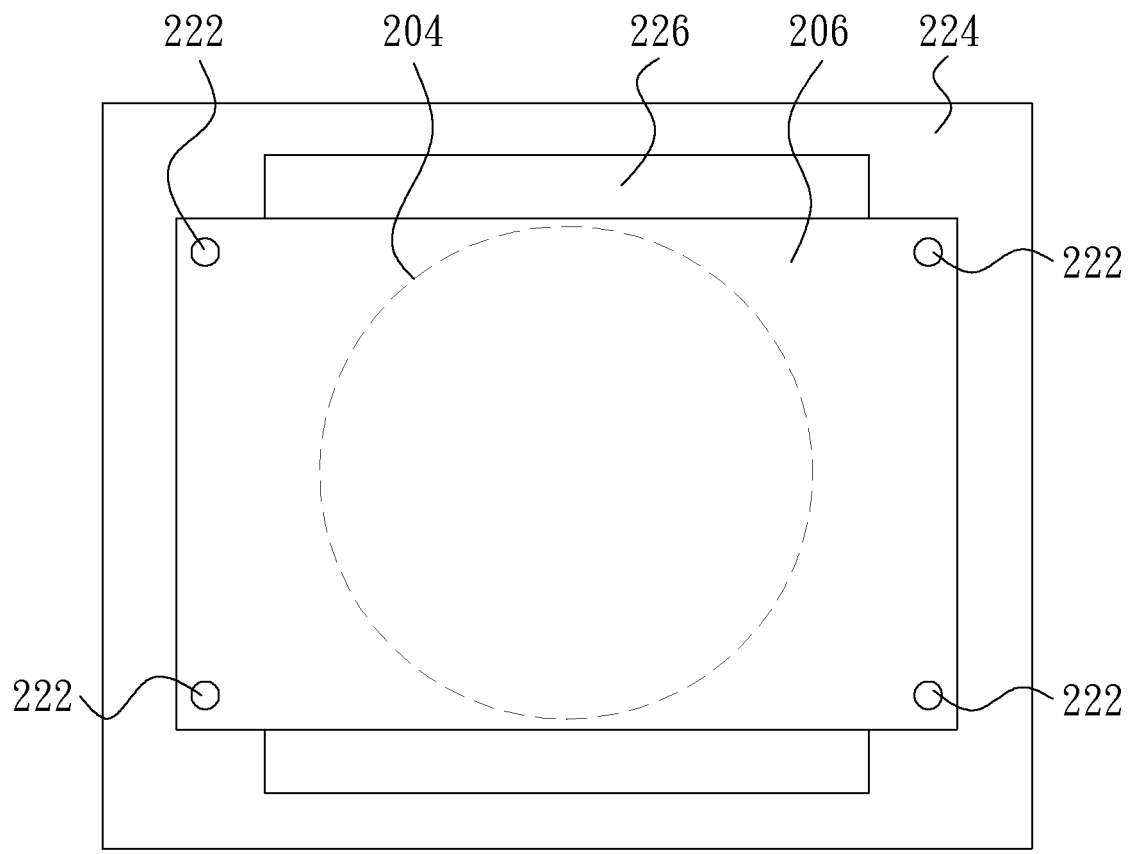
FIG. 5 is a schematic diagrammatic representation of a top view of the new designed operation stage illustrated in FIG. 4 that sustains a thee-down reticle or wafer to be inspected.

FIG. 4 is a schematic diagrammatic representation of another aimed-up charged particle beam system 200A in accordance with another embodiment of the present invention. FIG. 5 is a schematic diagrammatic representation of a top view of an operation stage that sustains a face-down reticle or wafer to be inspected in accordance with an embodiment of the present invention as illustrated in FIG. 4. Referring to FIG. 4 and FIG. 5, the aimed-up charged particle beam system 200A and the aimed-up charged particle beam system 200 have similar configurations, but they have different designs for moving the operation stage. The aimed-up charged particle beam system 200A includes all the aimed-up charged particle beam system 200 has, such as the electron source 216 configured at the bottom of the aimed-up charged particle beam system 200A for providing a primary beam upward, the condenser lens 214, the detector 212, the objective lens 210 and the operation stage 206 configured at the top of the aimed-up charged particle beam system 200A for holding the specimen 208 facing downward to the primary beam. The operation stage 206 is configured at the top of the aimed-up charged particle beam system 200A for holding the specimen 208, such as a reticle or a wafer, upside down and the inspected surface of the specimen 208 facing downward to the primary beam, such that particles nearby will not drop to the inspected surface of the specimen 208. A moving stage 224 is configured at the bottom of the aimed-up charged particle beam system 200A for moving the operation stage 206 on X, Y, and Z direction. The moving stage 224 has an opening 226 to provide a space surrounding the system 200A or the column 204. The space prevents the system 200A or the column 204 from colliding with the moving stage 224 when the moving stage 224 is moved. The supporting means 222 is mounted on the moving stage 224, and the operation stage 206 are supported by the supporting means 222. The operation stage 206 is configured at the top of the system 200A and above the moving stage 224 by the supporting means 222. The supporting means 222 may include several pillars (at least three pillars), for example three pillars, four pillars or more, or the supporting means may be a hollow cylinder which the aimed-up charged particle beam system 200A (including the vacuum chamber 202 and column 204) are configured inside. The moving stage 224 moves freely on X, Y, and Z direction by some devices, for example X direction sliders, Y direction sliders, elevator, etc., during operation. Therefore, the moving stage 224 can carry the operation stage 206 to move freely on X, Y, and Z direction.

Figure 6:
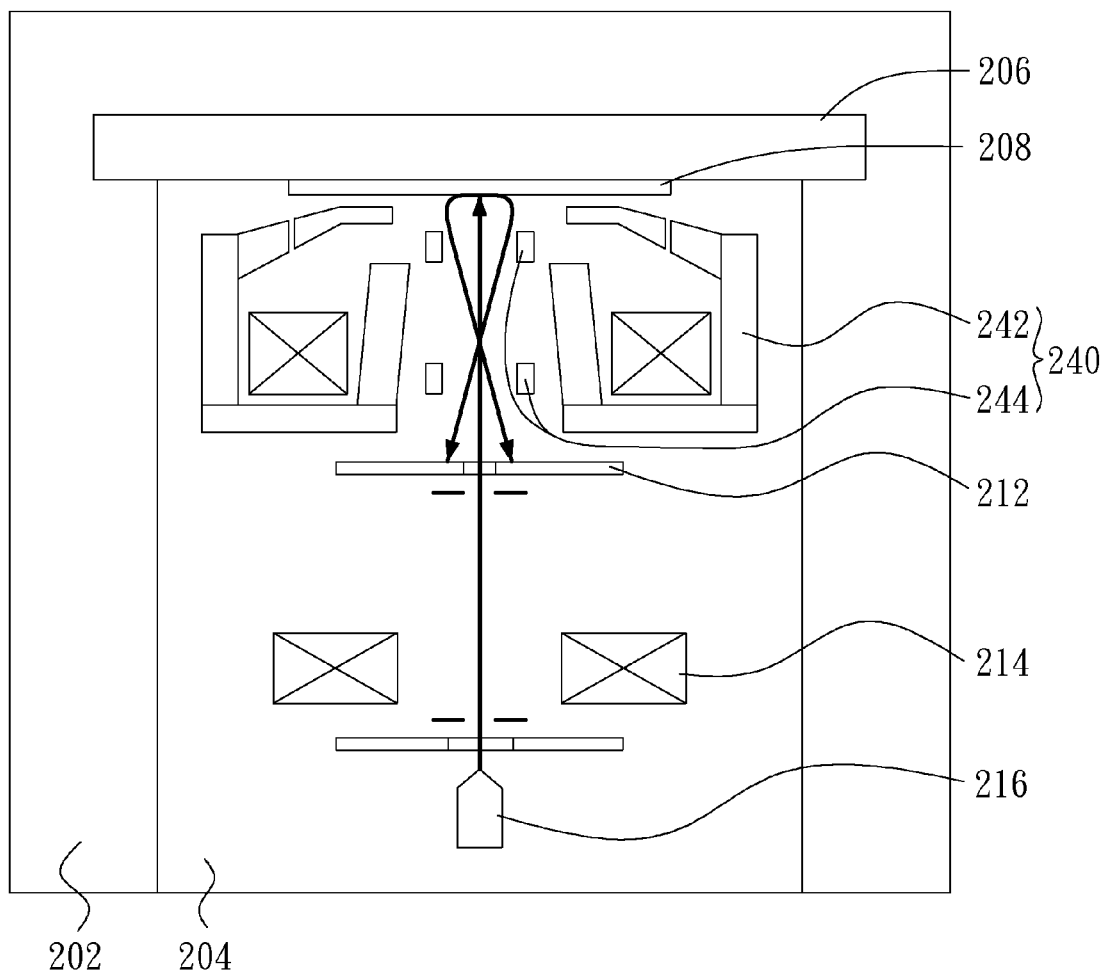
FIG. 6 is a schematic diagrammatic representation of an aimed-up charged particle beam system configured with a SORIL lens in accordance with an embodiment of the present invention.

Furthermore, the present invention provides an aimed-up charged particle beam system with a SORIL lens column, for example a SORIL SEM. Referring to FIG. 6, it is an aimed-up charged particle beam system 200B configured with a SORIL lens 240 in accordance with an embodiment of the present invention. The aimed-up charged particle beam system 200B includes an electron source 216, a condenser lens 214, a detector 212, a SORIL objective lens 240, and an operation stage 206. The electron source 216 is configured at the bottom of the aimed-up charged particle beam system 200B for providing a primary beam upward. The operation stage 206 is configured at the top of the aimed-up charged particle beam system 200B for holding a specimen 208, such as a reticle or a wafer, upside down and for holding the inspected surface of the specimen 208 facing downward to the primary beam, such that particles nearby will not drop to the critical surface of the specimen 208. The face down design may prevent AMC from gravitationally settling during inspection, thereafter having a cleaner result compared with conventional face-up inspection system. The condenser lens 214, the detector 212, and the SORIL objective lens 240 are configured between the electron source 216 and the operation stage 206. The SORIL objective lens 240 has a magnetic lens 242 and an electrostatic lens. Furthermore, the SORIL, objective lens 240 has a deflector 244 inside the SORIL objective lens 240. The electron source 216, the condenser lens 214, the detector 212, and the SORIL objective lens 240 (including the magnetic lens 242, the electrostatic lens and the deflector 244) are configured inside a column 204 to form so-called SORIL lens column 204. The electron source 216, the condenser lens 214, the detector 212, the SORIL objective lens 240 (including the magnetic lens 242, the electrostatic lens and the deflector 244), and the operation stage 206 are inside a vacuum chamber 202 for reducing the particles in the system 200B. The column 204 is inside the vacuum chamber 202, and both of the column 204 and the vacuum chamber 202 are in a vacuum environment. The aimed-up charged particle beam system 200B provides a vacuum environment during inspection. Therefore, the gravitational settling of AMC during inspection can be avoided. The primary beam is aimed up to the face-downed specimen (or inspected object), wherein the specimen (or inspected object) is a wafer, a reticle for regular lithography or an EUV mask. The system 200B can adopt the design illustrated in FIG. 3 or the design illustrated in FIG. 5 for moving the operation stage 206 freely on X direction and Y direction.

Figure 7:
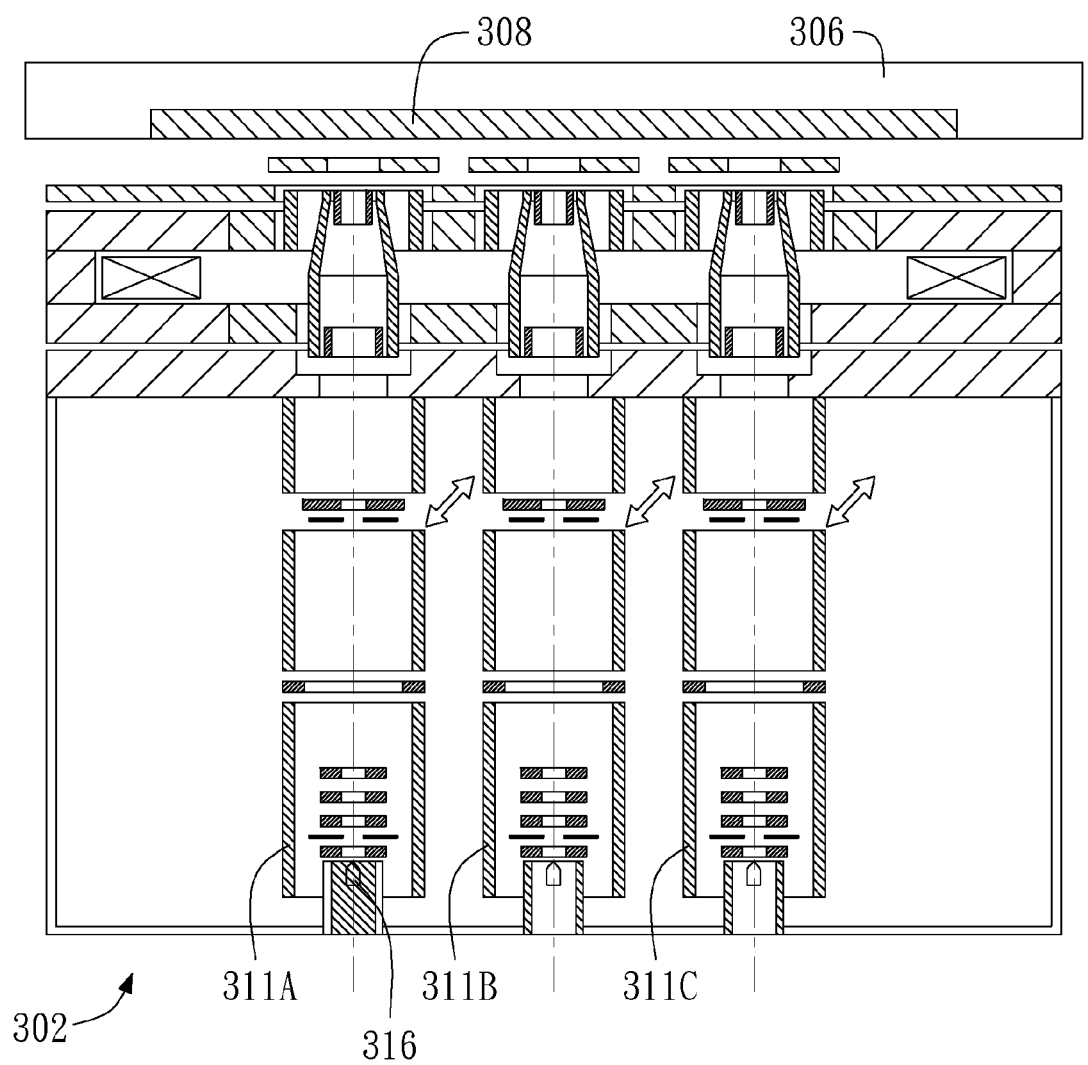
FIG. 7 is a schematic diagrammatic representation of an aimed-up charged particle beam system configured with a multi-axial objective lens in accordance with an embodiment of the present invention.

Furthermore, the present invention provides an aimed-up charged particle beam system configured with a multi-axial objective lens (columns). Referring to FIG. 7, it is a schematic diagrammatic representation of an aimed-up charged particle beam system 300 configured with a multi-axial objective lens (columns) in accordance with an embodiment of the present invention. The aimed-up charged particle beam system 300 has three objective lens columns 311A, 311B and 311C. Each of the objective lens columns 311A, 311B and 311C includes all the column 204 (shown in FIG. 2 or FIG. 4) has, such as electron source providing a primary beam upward, condenser lens, detector, aperture, deflector, and objective lens (or SORIL objective lens). Primary beams emitted from different electron sources 316 of objective lens columns 311A, 311B and 311C are aimed up to different areas on the inspected surface of the face-downed specimen 308 at the same time. Therefore, the system 300 can inspect several different areas on the inspected surface of the specimen 308 at the same time. The specimen (or inspected object) 308 is a wafer, a reticle for regular lithography or an EUV mask. All Objective lens columns 311A, 311B and 311C and the operation stage 306 are inside the vacuum chamber 302 for reducing the particles in the system 300.

Figure 8:
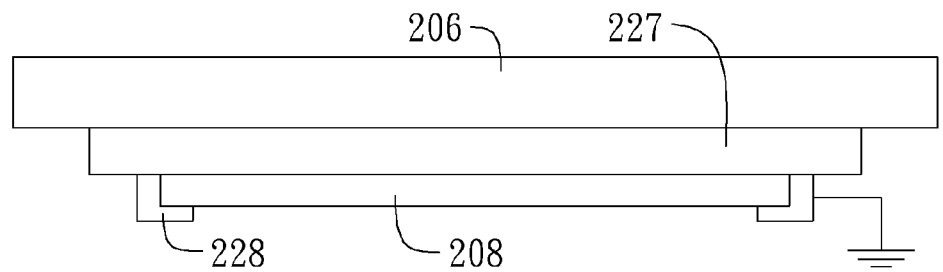
FIG. 8 is a schematic diagrammatic representation of an adaptor in accordance with an embodiment of the present invention.

In the present invention, the operation stage of the aimed-up charged particle beam system illustrated in all embodiments has an adaptor for holding the specimen upside down and for holding the inspected surface of the specimen facing downward to the primary beam. Referring to FIG. 8, it is a schematic diagrammatic representation of an adaptor 227 in accordance with an embodiment of the present invention. The adaptor 227 is configured on the operation stage (as shown in FIGS. 2-7), and more particularly, on the surface of operation stage facing the electron source. The adaptor 227 can hold the reticle or wafer facing down mechanically or electro-statically during inspection. The adaptor 227 may be a mechanical adaptor or electro-statical adaptor, for example an e-chuck, or other adaptor for mechanically or electro-statically holding the reticle or wafer 208 facing down during inspection. A clamping ring 228 is configured on the adaptor for preventing specimen 208 from downfall. The clamping ring 228 is electrically coupled to ground for removing the charge on the inspected surface of the specimen 208 during inspection.

Figure 9A:
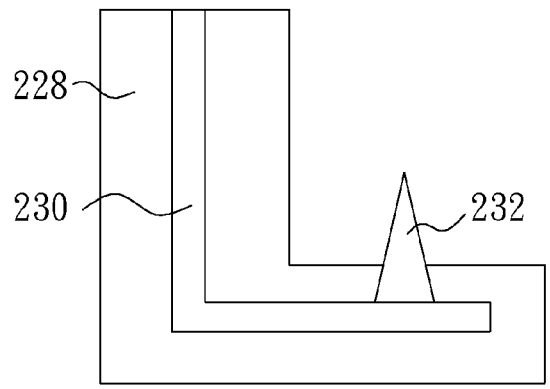
FIG. 9A is a schematic diagrammatic representation of a clamping ring on the adaptor in accordance with an embodiment of the present invention.
Figure 9B:
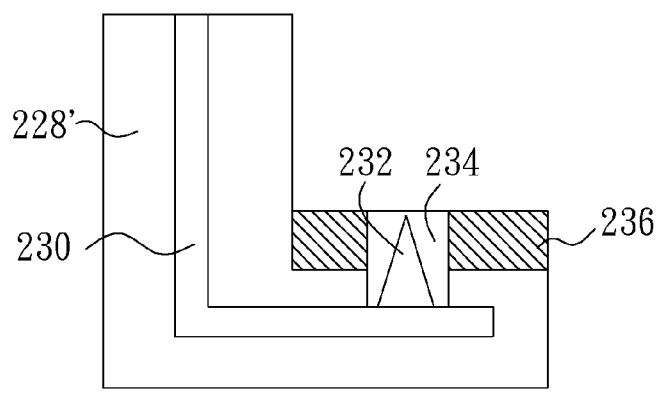
FIG. 9B is a schematic diagrammatic representation of another clamping ring on the adaptor in accordance with another embodiment of the present invention.

Referring to FIG. 9A, it is schematic diagrammatic representation of a clamping ring 228 on the adaptor in accordance with an embodiment of the present invention. The clamping ring 228 has a pin 232 and a wire 230 inside the clamping ring 228. Tip of the pin 232 protrude from the surface of the clamping ring 228 for contacting and electrically coupling the specimen during inspection. The wire 230 electrically couples the pin 232 to ground. Therefore, the specimen electrically couples ground to the pin 232 and the wire 230 during inspection for removing the charge on the surface of the specimen during inspection. Furthermore, the present invention provides another type of clamping ring. Referring to FIG. 9B, it is schematic diagrammatic representation of a clamping ring 228' on the adaptor in accordance with another embodiment of the present invention. The clamping ring 228' has similar structure to the clamping ring 228, but the clamping ring 228' has a conductive rubber pad 236 on the clamping ring 228'. The conductive rubber pad 236 and the clamping ring 228' have a hole 234 that sustains the pin 232 inside the hole 234, and therefore, tip of the pin 232 will not protrude from the surface of the clamping ring 228' for protecting the pin 232 before the adaptor holds the specimen. The conductive rubber pad 236 is made of an elastic material. Therefore, when adaptor picks up or holds a specimen, the conductive rubber pad 236 is compressed and thereafter the pin 232 will protrude from the conductive rubber pad 236 to contact the specimen. At this time, the pin 232 and the wire 230 electrically couple the specimen to ground for removing the charge on the surface of the specimen during inspection.

In the present invention, the adaptor, even the operation stage needs to move out the vacuum chamber for loading and unloading the specimen. When loading the specimen, the adaptor or the operation stage is moved out by a robot and put on the specimen for picking up and holding the specimen. When unloading the specimen, the adaptor or the operation stage is moved out by a robot and put on an unload port for placing the specimen on the unload port.

One of the advantages of the upside down column and the primary beam aimed-up design is that the system is made stable. The gravity center of the system is lower and closer to the floor than conventional design. Another of the advantages of the upside down column and the primary beam aimed-up design is that gravitational settling of AMC during inspection can be avoided and it has a cleaner result compared with conventional face-up inspection system.

The other embodiment of the present invention that equip the upside down inspection system with multi-axial lens column to gain throughput in addition to the benefit of prevent AMC contamination during inspection.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the invention as limited only by the appended claims.

What is claimed is:

1. An aimed-up charged particle beam system, comprising:
   an electron source providing a primary beam upward;
   a condenser lens, over the electron source, for condensing the primary beam;
   an objective lens, over the condenser lens, for focusing the primary beam to a surface of a specimen; and
   an operation stage for holding the specimen upside down and the surface of the specimen facing downward to the primary beam, such that particles nearby will not drop to the surface of the specimen.

2. The aimed-up charged particle beam system of claim 1, further comprising a detector between the objective lens and the condenser lens.

3. The aimed-up charged particle beam system of claim 2, wherein the electron source, condenser lens, detector, objective lens, and operation stage are inside a vacuum chamber.

4. The aimed-up charged particle beam system of claim 3, wherein the electron source, condenser lens, detector, and objective lens are inside a column.

5. The aimed-up charged particle beam system of claim 3, wherein aimed-up charged particle beam system comprises a plurality of columns and each of columns comprises the electron source, condenser lens, detector, and objective lens therein.

6. The aimed-up charged particle beam system of claim 2, wherein the aimed-up charged particle beam system is a SORIL SEM.

7. The aimed-up charged particle beam system of claim 2, wherein the objective lens includes a magnetic lens and an electrostatic lens.

8. The aimed-up charged particle beam system of claim 7, wherein the objective lens includes a deflector inside the objective lens.

9. The aimed-up charged particle beam system of claim 2, wherein the detector receives secondary electrons emanating from the surface of the specimen.

10. The aimed-up charged particle beam system of claim 2, wherein the electron source is configured at the bottom of the aimed-up charged particle beam system.

11. The aimed-up charged particle beam system of claim 10, wherein the operation stage is configured at the top of the aimed-up charged particle beam system.

12. The aimed-up charged particle beam system of claim 11, further comprising a supporting means for supporting the operation stage at the top of the aimed-up charged particle beam system.

13. The aimed-up charged particle beam system of claim 12, wherein the supporting means comprises at least three pillars.

14. The aimed-up charged particle beam system of claim 12, wherein the supporting means is a cylinder.

15. The aimed-up charged particle beam system of claim 14, wherein the electron source, condenser lens, detector, and objective lens are inside a vacuum chamber or a column; and the vacuum chamber or the column is inside the cylinder.

16. The aimed-up charged particle beam system of claim 12, further comprising a moving stage configured at the bottom of the aimed-up charged particle beam system for moving the operation stage on X, Y, and Z direction.

17. The aimed-up charged particle beam system of claim 16, wherein the operation stage is supported over the moving stage by the supporting means.

18. The aimed-up charged particle beam system of claim 11, further comprising a pair of X direction sliders configured at the top of the aimed-up charged particle beam system for moving the operation stage on X direction.

19. The aimed-up charged particle beam system of claim 11, further comprising a pair of Y direction sliders configured at the top of the aimed-up charged particle beam system for moving the operation stage on Y direction.

20. The aimed-up charged particle beam system of claim 1, further comprising an adaptor configured on the operation stage for holding the specimen upside down and the surface of the specimen facing downward to the primary beam.

21. The aimed-up charged particle beam system of claim 20, further comprising a clamping ring configured on the adaptor for preventing specimen from downfall.

22. The aimed-up charged particle beam system of claim 21, further comprising a pin in the clamping ring for electrically coupling the specimen to ground during inspection.

* * * * *